US007785822B2

(12) United States Patent
Gregory et al.

(10) Patent No.: US 7,785,822 B2
(45) Date of Patent: Aug. 31, 2010

(54) ASSAYS FOR THE DETECTION OF BILIVERDIN IN BIRDS AND REPTILES

(75) Inventors: Christopher Gregory, Nicholson, GA (US); Branson W. Ritchie, Athens, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 1251 days.

(21) Appl. No.: 10/525,893

(22) PCT Filed: Aug. 27, 2003

(86) PCT No.: PCT/US03/27134

§ 371 (c)(1), (2), (4) Date: Jul. 8, 2005

(87) PCT Pub. No.: WO2004/020980

PCT Pub. Date: Mar. 11, 2004

(65) Prior Publication Data

US 2006/0252110 A1 Nov. 9, 2006

Related U.S. Application Data

(60) Provisional application No. 60/406,175, filed on Aug. 27, 2002.

(51) Int. Cl.
*C12N 5/07* (2010.01)
*C12N 5/10* (2010.01)
*C12Q 1/00* (2006.01)

(52) U.S. Cl. .............................. 435/25; 435/4; 435/349; 435/967

(58) Field of Classification Search ........................ None
See application file for complete search history.

(56) References Cited

U.S. PATENT DOCUMENTS 5,284,940 A 2/1994 Lin et al.

5,783,407 A * 7/1998 Yein et al. ...................... 435/25
6,902,881 B2 * 6/2005 Falchuk ...................... 435/1.1

OTHER PUBLICATIONS

Derwent Abstract, Acc. No. 1987-173702, see entire abstract, 1987.*
Conrelius, "Biliverdin in biological systems," *One Medicine: A Tribute to Kurt Benirschkle*, Ryder et al. eds., Springer-Verlag, Berlin, pp. 321-335, 1984.
Cunningham et al., "Studies on the Specificity of the Tetrapyrrole Substrate for Humam Biliverdin-IXα Reductase and Biliverdin-IXβ Reductase," *Journal of Biological Chemistry*, 275(25) pp. 19009-19017 (Jun. 23, 2000).
Ennis et al., "Cloning and Overexpression of Rat Kidney Biliverdin IXα Reductase as a Fusion Protein with Glutathione S-transferase: Steriochemistry of NADH Oxidation and Evidence that the Presence of the Glutathione S-transferase Domain does not effect BVR-A Activity," *Biochem J.*, 328, 33-36 (1997).
Fakhrai et al., "Expression and Characterization of a cDNA for Rat Kidney Biliverdin Reductase," *J Biol Chem*, 267:6, 4203-4029 (1992).
Harr et al., "Clinical Chemistry of Companion Avian Species: A Review," *Veteran Clinical Pathology* 31(3), 140-151. (Jan. 1, 2002).
Itoh et al., "Relationships Between Serum (ZZ)-Bilirubin, its Subfractions and Biliverdin Concentrations in Infants at 1-month Check-ups," Ann *Clin Biochem* 38(4), 323-328 (Jul. 1, 2001).
Kaneko, "Hemoglobin Synthesis and Destruction," *Schlam's Veterinary Hematology* Feldman et al ed., Lippincoott, Williams, and Williams, Philadelphia, pp. 135-139, 2000.
Kutty et al., "Purification and Characterization of Bilverdin Reductase from Rat Liver." *J Biol Chem*, 256(8), 3956-3962 (Apr. 25, 1981).
Lumeij, "Avian Clinical Biochemistry," *Clinical Biochemistry of Domestic Animals Kaneko* et al eds., Academic Press, San Diego, pp. 857, 869-871, 1997.
Walters et al., "An ultramicromethod for the determination of conjugated and total bilirubin in serum or plasma," *Microchem. J*, 15:231, 1970.
Winsten et al., "A Rapid Diazo Technique for Measuring Total Bilirubin," *Clin Chim Acta*, 25(3), 441-446 (Sep. 1, 1969).

* cited by examiner

*Primary Examiner*—David M. Naff
*Assistant Examiner*—Debbie K Ware
(74) *Attorney, Agent, or Firm*—Ballard Spahr LLP (57) ABSTRACT

The present invention provides methods for the detection of biliverdin in birds (avian species) and reptiles.

19 Claims, 6 Drawing Sheets

ASSAYS FOR THE DETECTION OF BILIVERDIN IN BIRDS AND REPTILES

This application is a National Stage under 35 U.S.C. 371 of International Application No. PCT/US2003/027134, filed Aug. 27, 2003, published in English as International Publication Number WO 2004/020980 A2 on Mar. 11, 2004, which claims priority to, and the benefit under U.S.C. 119(e) of, U.S. Provisional Patent Application No. 60/406,175, filed Aug. 27, 2002, which is hereby incorporated by reference in its entirety.

FIELD OF THE INVENTION

The present invention relates to assays for the detection of biliverdin in birds (avian species) and reptiles.

BACKGROUND OF THE INVENTION

Birds and reptiles commonly present with clinical illness related to liver disease. Biochemical tests, such as serum enzyme activities and bile acid concentrations, have been used for the antemortem diagnosis of liver disease in birds and reptiles, but these tests have clinical limitations.

In mammals, bilirubin quantitation is used to assess increased erythrocytic destruction and cholestasis. Hyperbilirubinemia is often observed in liver and hemolytic diseases. Therefore, total, conjugated, and unconjugated serum bilirubin concentrations and the presence or absence of bilirubinuria are used routinely in mammals as screening tests for hepatic function or extrahepatic disease. Liver diseases associated with hepatocellular swelling, hepatic fibrosis, hepatic inflammation or extrahepatic diseases resulting in red cell hemolysis, bile duct inflammation or obstruction may cause hyperbilirubinuria and bilirubinuria. The measurement of conjugated bilirubin in urine is of value in mammals because bilirubinuria often precedes the onset of hyperbilirubinemia. Measuring the serum concentrations of conjugated and unconjugated bilirubin can aid in differentiating extrahepatic from intrahepatic disease in mammals.

Birds and reptiles lack biliverdin reductase, the enzyme responsible for conversion of biliverdin to bilirubin; therefore, they do not produce bilirubin. In birds and reptiles, biliverdin (not bilirubin) is the waste product of hemoglobin destruction. Since bilirubin is not usually present in avian and reptile serum and urine, its measurement is not useful in evaluating liver disease or hemolytic disease in birds. The majority of biliverdin is excreted in an unconjugated form into the bile. Blood biliverdin concentration increases when hepatic regurgitation due to decreased function or biliary obstruction occurs, resulting in the typical green discoloration of plasma or urine.

The present invention provides a biochemical assay to quantitate the biliverdin present in plasma, serum or biological fluids collected from birds and reptiles. This test will prove of benefit as an adjunct to serum enzyme activities and bile acid concentrations in evaluating intra- and extrahepatic diseases in birds and reptiles.

SUMMARY OF THE INVENTION

The present invention provides a method of determining biliverdin concentration in a sample from an avian or reptilian species comprising: a) contacting the sample with biliverdin reductase; b) measuring a change in absorbance at about 325 nm to about 500 nm; and c) determining biliverdin concentration by comparing the absorbance value obtained in step b) with absorbance values on a standard concentration curve.

The present invention also provides a method of measuring increased biliverdin concentration in a sample from an avian or reptilian species comprising: a) contacting the sample with biliverdin reductase; and b) measuring a change in absorbance at about 325 nm to about 500 nm, wherein a change in absorbance as compared to a control sample indicates increased biliverdin concentration in the sample.

The present invention further provides a method of measuring above-normal levels of biliverdin concentration in a sample from an avian or reptilian species comprising: a) contacting the sample with biliverdin reductase; and b) measuring a change in absorbance at about 325 nm to about 500 nm, wherein a change in absorbance as compared to values obtained from a control sample indicates an above-normal biliverdin concentration in the sample.

Also provided by the present invention is a method of determining biliverdin concentration in a sample from an avian or reptilian species comprising: a) contacting the sample with biliverdin reductase; b) measuring a change in absorbance at about 500 nm to about 750 nm; and c) determining biliverdin concentration by comparing the absorbance value obtained in step b) with absorbance values on a standard concentration curve.

The present invention provides a method of measuring increased biliverdin concentration in a sample from an avian or reptilian species comprising: a) contacting the sample with biliverdin reductase; and b) measuring a change in absorbance at about 500 nm to about 750 nm, wherein a change in absorbance as compared to a control sample indicates increased biliverdin concentration in the sample.

The present invention provides a method of measuring above-normal levels of biliverdin concentration in a sample from an avian or reptilian species comprising: a) contacting the sample with biliverdin reductase; and b) measuring a change in absorbance at about 500 nm to about 750 nm, wherein a change in absorbance as compared to values obtained from a control sample indicates above-normal biliverdin concentration in the sample.

The present invention also provides a kit for measuring biliverdin concentration comprising biliverdin reductase.

DETAILED DESCRIPTION OF THE INVENTION

The present invention may be understood more readily by reference to the following detailed description of the preferred embodiments of the invention and the Example included herein.

Before the present compounds and methods are disclosed and described, it is to be understood that this invention is not limited to specific methods, as such may, of course, vary. It is also to be understood that the terminology used herein is for the purpose of describing particular embodiments only and is not intended to be limiting.

It must be noted that, as used in the specification and the appended claims, the singular forms "a," "an," and "the" include plural referents unless the context clearly dictates otherwise.

The present invention provides a method of measuring increased biliverdin concentration in a sample from an avian or reptilian species comprising: a) contacting the sample with biliverdin reductase; and b) measuring a change in absorbance at about 325 nm to about 500 nm, wherein a change in absorbance as compared to a control sample indicates increased biliverdin concentration in the sample.

Also provided by this invention is a method of measuring increased biliverdin concentration in a sample from an avian or reptilian species comprising: a) contacting the sample with biliverdin reductase; and b) measuring a change in absorbance at about 500 nm to about 750 nm, wherein a change in absorbance as compared to a control sample indicates increased biliverdin concentration in the sample.

The present invention provides a method of measuring decreased biliverdin concentration in a sample from an avian or reptilian species comprising: a) contacting the sample with biliverdin reductase; and b) measuring a change in absorbance at about 325 nm to about 500 nm, wherein a change in absorbance as compared to a control sample indicates decreased biliverdin concentration in the sample.

Also provided by this invention is a method of measuring decreased biliverdin concentration in a sample from an avian or reptilian species comprising: a) contacting the sample with biliverdin reductase; and b) measuring a change in absorbance at about 500 nm to about 750 nm, wherein a change in absorbance as compared to a control sample indicates decreased biliverdin concentration in the sample.

The test samples of the present invention can be obtained directly from an avian or reptilian species or obtained from other sources. The control sample can be obtained directly from a control animal or purchased from a commercial source. One of skill in the art can utilize the methods of the present invention to analyze samples that are obtained by the skilled artisan or to analyze samples that are obtained by other parties and later provided to the skilled artisan.

The avian species from which samples can be obtained include, but are not limited to, *Tinamiformes* (tinamous), *Struthioniformes* (ostrich and allies), *Podicipediformes* (grebes), *Sphenisciformes* (penguins), *Procellariiformes* (albatrosses and fulmars), *Pelecaniformes* (cormorants and pelicans), *Anseriformes* (waterfowl, e.g. ducks, geese, swans), *Phoenicopteriformes* (flamingos), *Ciconiiformes* (herons, storks, New World vultures and relatives), *Falconiformes* (hawks and vultures), *Galliformes* (domestic fowl and game birds), *Gruiformes* (cranes, hemipodes, gallinules), *Charadriiformes* (gulls and shore birds), *Gaviiformes* (divers, loons), *Columbiformes* (doves and pigeons), *Psittaciformes* (parrots), *Coliiformes* (mousebirds), *Musophagiformes* (turacos), *Cuculiformes* (cuckoos), *Strigiformes* (owls), *Caprimulgiformes* (goatsuckers), *Apodiformes* (swifts and hummingbirds), *Trogoniformes* (trogons), *Coraciiformes* (rollers, kingfishers and relatives), *Piciformes* (woodpeckers, toucans and relatives), *Passeriformes* (songbirds, or passerines and perching birds).

The reptiles from which samples can be obtained include, but are not limited to, *Crocodylidae* (Caiman and Crocodiles), *Squamata* Suborder *Amphisbaenia* (Worm-Lizards), *Amphisbaenidae* Family (Worm-Lizards), Suborder *Sauria* (Lacertilia) (Lizards), *Anguidae* Family (Alligator Lizards), *Corytophanidae* Family (Basilisks), *Gekkonidae* Family (Geckos), *Iguanidae* Family (Iguanas), *Phrynosomatidae* Family (Spiny Lizards), *Polychrotidae* Family (Anoles), *Scincidae* Family (Skinks), *Teiidae* Family (Whip-tailed Lizards), *Xantusiidae* Family (Night Lizards), Suborder *Serpentes* (Ophidia) (Snakes), *Anomalepididae* Family (Dawn Blind Snakes), *Boidae* Family (Boas), *Colubridae* Family (Harmless Snakes), *Elapidae* Family (Coral Snakes), *Hydrophiidae* Family (Sea Snakes), *Leptotyphlopidae* Family (Thread Snakes), *Viperidae* Family (Vipers), Order *Testudinata* (Chelonia) (Turtles and Tortoises), Suborder *Cryptodira* (Hidden-Necked Turtles), *Cheloniidae* Family (Sea Turtles), *Chelydridae* Family (Snapping Turtles), *Deromchelyidae* Family (Leatherback Sea Turtle), *Emydidae* Family (Pond and River Turtles), *Kinosternidae* Family (Mud and Musk Turtles), *Testudinidae* Family (Tortoises).

The sample of this invention can be from any bird or reptile and can be, but is not limited to, plasma, serum, urine, peripheral blood, sputum, fine needle aspirations or other biological fluids.

As mentioned above, biliverdin reductase is an enzyme responsible for the conversion of biliverdin to bilirubin. Therefore, by contacting biological samples with biliverdin reductase, any biliverdin present in the sample should be converted to bilirubin, thus allowing one of skill in the art to measure the amount of biliverdin present in the sample by measuring the change in absorbance at about 325 to about 750 nm. For example, wavelengths of about 325, 350, 375, 400, 425, 450, 475, 500, 525, 550, 575, 600, 625, 650, 675, 700, 725 and 750 can be utilized. One of skill in the art can utilize any wavelength between about 325 nm and 750 nm that results in changes in absorbance corresponding to the measurement of biliverdin concentration or bilirubin production. For instance, as set forth in the Examples herein, at certain wavelengths, one of skill in the art will observe an increase in absorption that corresponds to increased bilirubin production. At other wavelengths, one of skill in the art will observe decreased absorption corresponding to decreased biliverdin concentrations. Biliverdin reductase can be obtained from commercial sources such as ICN Biochemicals or the enzyme can be cloned and produced by standard recombinant methods as described in the Examples herein. The biliverdin reductase can be from rat, mouse, human or other mammalian origin. One of skill in the art can determine the specific activity of a recombinant biliverdin reductase preparation as well as the concentration of biliverdin reductase necessary for conversion of biliverdin to bilirubin. The preparation can be such that no other bacterial proteins or other contaminants are present in the preparation or the preparation can be purified such that all or most bacterial proteins are removed.

The contacting step of the methods described herein can be performed in any order. For example, biliverdin reductase can be added to a sample in a microcuvette or other sample container, or the sample can be added to biliverdin reductase present in a microcuvette or other sample container.

By utilizing the methods of the present invention, one of skill in the art can measure increased biliverdin concentration in a particular bird or reptile. For example, a sample can be obtained from a bird or reptile. This sample is then contacted with biliverdin reductase and a change in absorbance is measured as described in the Examples. Although there are numerous methods known in the art for the measurement of changes in absorbance, the sample of the present invention can be contacted with biliverdin reductase and a change in absorbance at two fixed times (two point kinetic assay) or a continual monitoring of the change in absorbance (absorbance/minute) can be performed as described in the Examples. This change in absorbance is compared with the change in absorbance in a control sample. The control sample can be a sample from a bird or reptile with normal levels of biliverdin. One of skill in the art can utilize the methods of the present invention to determine reference levels or a range of biliverdin concentration corresponding to a particular avian or reptilian species. One of skill in the art can also utilize reference values established for a particular avian or reptilian species. These values can then be compared to biliverdin concentration in test samples to determine whether or not there is increased biliverdin concentration or an amount of biliverdin corresponding to a disease state. Once the skilled artisan compares the change in absorbance in the sample with the control sample, if the change in absorbance is greater or less in the sample, depending on the wavelength used to measure absorbance, the sample contains increased or elevated levels of biliverdin as compared to the biliverdin levels in a normal, non-diseased bird or reptile. These increased levels of biliverdin could indicate the presence of a disease state. In the methods of the present invention, any change in absorbance in a control sample that is not contacted with the biliverdin reductase can also be measured. Any change in absorbance observed with this sample can be subtracted from test values in order to eliminate background absorption unrelated to biliverdin reductase activity.

The present invention provides a method of measuring above-normal levels of biliverdin concentration in a sample from an avian or reptilian species comprising: a) contacting the sample with biliverdin reductase; and b) measuring a change in absorbance at about 325 nm to about 500 nm, wherein a change in absorbance as compared to values obtained from a control sample indicates above-normal biliverdin concentration in the sample.

The present invention also provides a method of measuring above-normal levels of biliverdin concentration in a sample from an avian or reptilian species comprising: a) contacting the sample with biliverdin reductase; and b) measuring a change in absorbance at about 500 nm to about 750 nm, wherein a change in absorbance as compared to values obtained from a control sample indicates above-normal biliverdin concentration in the sample.

The present invention provides a method of measuring below-normal levels of biliverdin concentration in a sample from an avian or reptilian species comprising: a) contacting the sample with biliverdin reductase; and b) measuring a change in absorbance at about 325 nm to about 500 nm, wherein a change in absorbance as compared to values obtained from a control sample indicates below-normal biliverdin concentration in the sample.

The present invention also provides a method of measuring below-normal levels of biliverdin concentration in a sample from an avian or reptilian species comprising: a) contacting the sample with biliverdin reductase; and b) measuring a change in absorbance at about 500 nm to about 750 nm, wherein a change in absorbance as compared to values obtained from a control sample indicates below-normal biliverdin concentration in the sample.

As described above, reference intervals or a range of biliverdin concentrations corresponding to a particular avian species or reptile can be established. These intervals can correspond to normal biliverdin levels. Therefore, one of skill in the art can compare a change in absorbance in a test sample with absorbance values obtained from a control sample and determine whether or not the change in absorbance as compared to the control sample corresponds to above or below normal biliverdin concentration in that species. One of skill in the art can also compare a biliverdin concentration obtained from a test sample with established reference biliverdin concentrations to determine whether or not the sample contains above or below normal levels of biliverdin concentration. For example, if a biliverdin concentration of 1.0 mg/dl is obtained for a test sample from a particular species and the normal biliverdin concentration for that species is 0.6 mg/dl, the test sample contains above-normal biliverdin concentration levels. Similarly, if the biliverdin concentration is 0.3 mg/dl and the normal biliverdin concentration is 0.6, the test sample contains below normal biliverdin concentration.

One of skill in the art could also utilize this method to monitor the health of a particular bird or reptile. For example, once a bird or reptile has been identified as having increased biliverdin levels, samples can be obtained from the same bird or reptile in the future and compared with previous samples from the same bird or reptile in order to determine the progression of the disease. For example, a sample obtained at a later date can be compared with a sample obtained previously. If the concentration is greater in the sample obtained at a later date as compared with the biliverdin concentration associated with the previous sample, this would indicate deteriorating health in the bird or reptile. Similarly, if biliverdin concentration is less in the sample obtained at a later date as compared with the biliverdin concentration associated with the previous sample, this would indicate improving health in the bird or reptile. Thus, a method of detecting decreased or below-normal levels of biliverdin is also provided by this invention. By utilizing these comparative studies, one of skill in the art can monitor drug efficacy as well.

The disease states that can be diagnosed and monitored utilizing the methods of the present invention include, but are not limited to, liver diseases such as hepatitis and those associated with hepatocellular swelling, hepatic fibrosis and/or hepatic inflammation. The disease states can be infectious (i.e. bacterial, viral, chlamydial, fungal, mycoplasmal or parasitic) as well as noninfectious (i.e., metabolic, circulatory, neoplastic, traumatic, nutritional, biochemical or toxic). The methods of the present invention can also be utilized to diagnose and/or monitor extrahepatic disease such as hematologic diseases (for example, hemolytic disease, both extravascular and intravascular or other inherited/acquired conditions that result in increased erythrocyte destruction and hemoglobin degradation). Other extrahepatic diseases such biliary tract occlusion resulting in decreased excretion of biliverdin via the biliary tract into the intestine can also be diagnosed and/or monitored utilizing the methods of the present invention.

The present invention also provides a method of determining biliverdin concentration in a sample from an avian or reptilian species comprising: a) contacting the sample with biliverdin reductase; b) measuring a change in absorbance at about 325 to about 500 nm; and; c) determining biliverdin concentration by comparing the absorbance value obtained in step b) with absorbance values on a standard concentration curve.

The present invention further provides a method of determining biliverdin concentration in a sample from an avian or reptilian species comprising: a) contacting the sample with biliverdin reductase; b) measuring a change in absorbance at about 500 to about 750 nm; and; c) determining biliverdin concentration by comparing the absorbance value obtained in step b) with absorbance values on a standard concentration curve.

In addition to measuring relative increases or decreases in biliverdin concentration, the present invention allows the determination of biliverdin concentrations in biological samples obtained from birds and reptiles. Upon measuring the change in absorbance for a particular sample, one of skill in the art can determine the concentration of biliverdin in the sample by calculating a standard curve of concentration (y-axis) vs. change in absorbance (x-axis), determining the "best fit" linear regression equation and using this equation to calculate biliverdin concentrations in biological samples from birds and reptiles. As described in the Examples, the change in absorption can be calculated over a fixed or continual time period. For example, the change in absorption can be measured between about 0.25 and about 1.25 minutes, between about 0.3 minutes and about 1.3 minutes, between about 0.40 minutes and about 1.4 minutes, between about 0.5 minutes and about 1.5 minutes. Other time periods are also contemplated by this invention as long as an accurate measure of biliverdin concentration results from the time period chosen. Based on the data provided herein, normal serum values appear to be about <0.5 mg/dl. Therefore, sample concentrations greater than about 0.5 mg/dl may indicate a disease state. The Examples herein provide numerous examples of standard curves utilized to determine biliverdin concentrations as well as the concentration values observed for several test samples.

By measuring biliverdin concentrations, a particular bird or reptile can be monitored. For example, if a sample yields a biliverdin concentration of 0.7 mg/dl and at a later time, a sample from the same bird or reptile yields a biliverdin concentration of 0.9 mg/dl, one of skill in the art would know that the disease had progressed. Alternatively, if a sample yields a biliverdin concentration of 0.7 mg/dl and at a later time, a sample from the same bird or reptile yields a biliverdin concentration of 0.4 mg/dl, one of skill in the art would know that the bird's condition had improved. These comparative methods can also be utilized to determine drug efficacy. By monitoring increases or decreases in biliverdin concentration after the administration of a drug, medication or therapy, the efficacy of a particular drug, medication or therapy can be determined.

One of skill in the art could obtain numerous samples from a number of different bird and reptile species in order to create ranges of biliverdin concentration values that can be correlated to a particular disease state. One skilled in the art will then be able to correlate the levels of biliverdin detected using the methods disclosed herein with a particular stage of disease, thus utilizing the detection method for prognostic purposes. The prognostic evaluation can determine what type of drug or medication to administer at different stages of disease depending on the amounts of biliverdin detected in the sample.

All of the methods described herein can be used in combination with other methods utilized to detect serum enzyme activities and bile acid concentrations to provide a panel of results that will aid in the diagnosis and prognosis of disease.

These methods can also be utilized in conjunction with visual inspection of a biological sample from a bird or reptile which can be pigmented due to the presence of biliverdin.

By utilizing the methods of the present invention, one of skill in the art could monitor the conversion of biliverdin to bilirubin over a time period and determine a particular time point in which the absorbance value at about 325-750 nm would be an accurate measure of the amount of biliverdin present in the sample. In this way, one of skill in the art could obtain absorbance values at a certain time after contacting the sample with bilirubin reductase and correlate it to a particular concentration of biliverdin.

In addition to the above-described methods, there are other assays that can be utilized to measure biliverdin levels in biological fluids. One of these involves using the basic assay of body fluids in which biliverdin is converted to bilirubin via biliverdin reductase in the presence of NADH or NADPH. In this method, the skilled artisan can measure the change in absorbance (typically at about 200-365 nm) as NADH or NADPH is converted to NAD. Biliverdin concentrations can then be determined as described herein and in the Examples, via the construction of a standard curve and subsequent comparison of the change in absorbance for the test sample with the values on the standard curve.

Since these assays are based on the conversion of biliverdin to bilirubin, one of skill in the art could also utilize commercially available reagents to measure converted biliverdin (i.e., newly formed bilirubin). These methods include urine and serum reagent strip/pad (dipstick) methodology and reagent kits based on the diazo method. The diazo method is described in Winsten and Cehelyk ("A rapid diazo technique for measuring total bilirubin," *Clin Chim. Acta* 25: 441 (1969)) and in Walters and Gerarde ("An ultramicromethod for the determination of conjugated and total bilirubin in serum or plasma," Microchem. J. 15:231 (1970)), both of which incorporated herein in their entireties by this reference.

The present invention further provides a kit for the detection of biliverdin in biological samples from birds or reptiles comprising biliverdin reductase enzyme.

Kits comprising biliverdin reductase and a phosphate buffer are also provided by this invention. Further provided by this invention is a kit comprising biliverdin reductase, phosphate buffer and NADH. Also provided by this invention is a kit comprising biliverdin reductase, phosphate buffer, NADH and biliverdin.

The phosphate buffers that can be utilized in the methods of the present invention can be the phosphate buffer described in the Examples or any buffer that supplies a source of phosphorous and maintains a pH compatible with biliverdin reductase enzyme activity. The pH can vary depending on the source of the biliverdin reductase and whether NADH or NADPH is used. For example, one of skill in the art can utilized used 0.1M Tris-HCl, pH 8.7, 100 uM NADPH and biliverdin reductase. Alternatively, one of skill in the art can use 100 mM sodium phosphate, pH 7.2, 705 uM NADH, and biliverdin reductase.

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention.

EXAMPLE I

Recombinant Rat Biliverdin Reductase

A. RNA Extraction and Amplification

Primers were designed to amplify a 969 base pair (bp) DNA product using rat biliverdin reductase sequence available from GenBank (accession no. NM_053850 and based on Ennis et al.). The sense primer, KPNBILIVF, was designed to contain a KPN I restriction site (underlined). The antisense primer, XBABILIVR, was designed to contain an XBA I restriction site (underlined).

KPNBILIVF
5'-GGGGTACCCCGAGTGAAGAGACCGGCATGGATGCCGAGC-3'

XBABILIVR
5'-GCTCTAGAGCGACATGTTCCATGGTAAGAGCTAAAGGTGA-3'

Mechanical disruption of rat liver and kidney tissue was performed using a Micro-mincer (BioSpec Products, Bartlesville, Okla.)-a comparable apparatus may be used.

Minced tissue was further homogenized with a QIAshredder (Qiagen, Inc. Valencia, Calif.).

RNA was extracted from the disrupted, homogenized tissue with an RNeasy Mini Kit (Qiagen, Inc. Valencia, Calif.) per manufacturer's instructions. Comparable methods also may be used.

A commercially available kit was used for RT-PCR (Titan One Tube RT-PCR Kit, Roche Molecular Biochemicals, Indianapolis, Ind.); comparable methods may be used. 1 µl (approximately. 1 ug/ul) of the extracted RNA is added to a 49 µl RT-PCR working solution containing:

29.5 µl of DEPC-treated $H_2O$
200 µM dNTPs (4 µl of 10 mM dNTP mix) (included in kit)
2 µM of each of the sense and antisense primers (1 µl of a 10 pmol/µl primer solution)
5 mM DTT solution (2.5 µl of 100 mM solution) (included in kit)
10 µl of 5× Buffer (included in kit)
1 ul of enzyme mix (included in kit)

Cycling Parameters:
Reverse transcription:
  1 cycle of 42 C for 30 min
Denaturation of RNA/cDNA hybrid:
  1 cycle of 94 C for 2 min
Amplification:
  1 cycle of 94 C for 2 min
  5 cycles of:
    94 C for 1 min
    50 C for 2 min
    68 C for 3 min
  35 cycles of:
    94 C for 30 sec
    55 C for 30 sec
    68 C for 3 min
  1 cycle of 68 C for 10 min Analysis of PCR Reactions The amplicon was analyzed on a 1% agarose gel containing a 1:10,000 dilution of SYBR Gold nucleic acid gel stain (Molecular Probes, Eugene, Oreg.).

Five µL PCR product plus 2 µL loading buffer was added to each well. The gel was transilluminated and visualized with UV light.

B. Cloning and Expression of Recombinant Rat Biliverdin Reductase

The 969 bp amplicon was excised from the gel and extracted from the agarose using a GenElute Agarose Spin Column (Sigma Chemical Co., St. Louis, Mo.). The DNA was precipitated by the addition of 2× volume of ethanol, 0.1×3M sodium acetate, and freezing at −70 C for 30 minutes. After centrifugation for 20 minutes at 12,000 rpm, the pellet was washed in 500 ul 70% ethanol, centrifuged for 10 minutes at 12,000 rpm, and air dried. The DNA subsequently was re-dissolved in 100 ul of DEPC-treated deionized sterile water to an approximate concentration of 1 ug/ul). 10 ul aliquots of the amplicon were added to tubes containing 1 unit each of restriction enzymes KPN I and XBA I (Roche Molecular Biochemicals, Indianapolis, Ind.). In addition, the expression vector pBAD/gIII B (Invitrogen, Carlsbad, Calif.) also was added to a KPN I/XBA I mixture and both samples were incubated at 37° C. for one hour and then electrophoresed on a 1% agarose gel containing 1/10,000 concentration of Sybr Gold. Bands were excised and processed as described above. Both products were reconstituted in 20 ul DEPC-treated deionized sterile water, approximate concentration 1 ug/ul. 10 ul of each solution was added to a 50 ul solution containing 1 unit T4 DNA ligase and buffer (Roche Molecular Biochemicals, Indianapolis, Ind.) and incubated for 16 hours at 4° C. Chemically competent *Escherichia coli* (TOP10F', Invitrogen, Carlsbad, Calif.) was transformed with the ligated pBAD/GIII B/recombinant rat biliverdin reductase ligation product and recombinant rat biliverdin reductase expression was induced with arabinose with modification of the manufacturer's instructions. The transformed bacteria were grown for 16 hours in 50 ml of LB broth containing 2% arabinose.

Crude purification of the protein was performed by pelleting the bacteria with centrifugation at 6,000 rpm for 10 minutes at 4° C. After decanting the supernatant, the bacterial pellet was resuspended in 1 ml lysis buffer (50 mM $NaH_2PO_4$, 300 mM NaCl, 5 mM imidazole, and 50 mM Tris HCl, pH 8.0) and sonicated. The sonicated mixture was centrifuged again at 6,000 rpm and the supernatant was transferred to a new tube.

The enzyme mixture was analyzed by SDS PAGE on a 12% Tris glycine polyacrylamide gel stained with Coomassie Brilliant Blue and detection of an approximately 37.5 kd band. Confirmation that the band was indeed recombinant rat biliverdin reductase was by Western blotting of using a commercially available rabbit anti-biliverdin reductase antibody (StressGen Biotechnologies Corp., Victoria, BC Canada). A commercially available recombinant rat biliverdin reductase (StressGen Biotechnologies Corp., Victoria, BC Canada) was used as a positive control. Negative controls were bacteria transformed with pBAD/GIII B plasmid without a DNA insert.

Kinetic Assay Using Recombinant Rat Biliverdin Reductase

The kinetic assay was performed on a Beckman DU-530 spectrophotometer (comparable spectrophotometers may be used). The assay is based on one used in references 2 (Kutty and Maines) and 3 (Fakhrai and Maines), both of which are incorporated herein by this reference in their entireties. Briefly, the change in absorbance at 450 nm is monitored for 2 minutes at room temperature. The value Δabs/min is determined using the measured interval from 0.25 to 1.25 minutes. A standard curve is used to determine sample concentration.

As mentioned throughout the specification, one of skill in the art can utilize other wavelengths and time periods as long as an accurate measure of biliverdin concentration is obtained.

Construction of a Standard Curve

Commercially available biliverdin dihydrochloride (BV; ICN Biomedicals Inc., Aurora, Ohio) is dissolved in 100% DMSO to a concentration of 2.5 g/dl.

Standard concentrations of 0.5, 1.0, 5.0, 10.0, 15.0, and 20.0 mg/dl of BV are made in commercially available chicken serum (Invitrogen, Carlsbad, Calif.)

Reagents used (modified and/or based on references 1 and 2):

Recombinant rat biliverdin reductase enzyme mix (BVR)

0.1M potassium phosphate buffer, pH 7.0 containing 0.1 mg/ml bovine serum albumin (KP buffer)

0.5 M NADH (ICN Biomedicals, Aurora, Ohio)

Kinetic assay:

125 ul of KP buffer is added to 160 ul of HPLC grade water and 37.5 ul of

BVR 50 ul of standard or unknown sample is added to the reagent mix 2.5 ul of 0.5M NADH is added to a microcuvette The reagent sample mix (372.5 ul) is added to the microcuvette and the sample is immediately blanked and the assay is begun. The standard curve is plotted on an absorbance vs. time standard curve and a regression equation with the highest $R^2$ value is determined. Unknown sample concentrations of biliverdin are determined using the regression equation.

TABLE 1

Standard curve and assay of "normal" serum

| Abs/min [measured] | Standard concentration mg/dl | Reported value |
|---|---|---|
| 0.0912 | 15 | standard |
| 0.0791 | 10 | standard |
| 0.0472 | 5 | standard |
| 0.0114 | 1 | standard |
| 0.0067 | 0.5 | standard |
| | Sample identification | |
| 0.0011 | 186194 10-12-01 | <0.5 |
| 0 | 187059 | <0.5 |
| 0 | loggerhead | <0.5 |
| 0.0028 | 190633 owl | <0.5 |
| 0 | 187129 heparin avian | <0.5 |
| 0.0048 | 172970 turtle | <0.5 |
| 0.0003 | 177753 tortoise | <0.5 |
| 0 | 177754 tortoise | <0.5 |
| 0.0002 | 167718 tortoise | <0.5 |
| 0.0013 | 190615 toucan | <0.5 |
| 0.0003 | 190630 owl | <0.5 |
| 0.004 | 190629 owl | <0.5 |
| 0 | 187053 macaw | <0.5 |
| 0.0026 | 190657 cockatoo | <0.5 |
| 0.0011 | 190628 owl | <0.5 |
| 0.001 | 141247 owl | <0.5 |
| 0 | 181097 lizard | <0.5 |
| 0.0331 | unknown 2 mg/dl | <0.5 |
| 0.0243 | unknown 1 mg/dl | <0.5 |
| 0.0489 | unknown 4 mg/dl | <0.5 |
| 0.0535 | unknown 6 mg/dl | <0.5 |
| 0.0107 | unknown 0.2 mg/dl | <0.5 |
| 0.0006 | unknown 0 mg/dl | <0.5 |

EXAMPLE II

Protocols for Endpoint (Two-Point) Kinetic Assays

Stock and standard solutions are made as described above. Briefly, commercially available biliverdin dihydrochloride (BV; ICN Biomedicals Inc., Aurora, Ohio) is dissolved in 100% DMSO to a concentration of 100 mg/dl. Standard concentrations of 0.5, 1.0, 5.0, 10.0, 15.0, and/or 20.0 mg/dl of BV are made in sterile deionized water or commercially available chicken serum (Invitrogen, Carlsbad, Calif.).

Reagents used:

BVR: Recombinant rat biliverdin reductase enzyme mix

KP buffer: 0.1M potassium phosphate buffer, pH 7.0 containing 0.1 mg/ml bovine serum albumin 0.5 M NADH (ICN Biomedicals, Aurora, Ohio)

Samples were composed of 100 ul of standard added to 90 ul of KP buffer and 100 ul of BVR. The initial absorbance was measured at a predetermined wavelength. Subsequently, 10 ul of 0.5M NADH was added to each sample. The samples were incubated at room temperature for approximately 1 hour in a humidified, light-protected (dark) chamber. After incubation, the final absorbance was determined at the same predetermined wavelength. A standard curve was plotted and the "best fit" regression curve and equation was determined. Subsequent biliverdin concentrations were calculated using the appropriate standard curve.

Comparison of Water vs. Chicken Serum as Diluents and Effects on Assay

The decreases in absorbances at 660 nm were measured. This assay detects decreases in biliverdin concentrations as biliverdin is reduced to bilirubin by the enzymatic reaction catalyzed by biliverdin reductase.

Protocol:

Standards: Serial dilutions of a 100 mg/dl solution of biliverdin are made, using water as the diluent.

A reagent blank containing 100 ul sterile deionized water, 90 ul KP buffer, and 100 ul recombinant rat biliverdin reductase enzyme mix (BVR) is used to zero the instrument at 660 nm. After blanking, the initial absorbance of each standard is measured at 660 nm. Each standard contains:

100 ul of standard 90 ul KP buffer 100 ul BVR

After the initial absorbance is measured (Table 1), 10 ul of 0.5 M NADH is added to each cuvette and the solution is gently mixed and incubated at room temperature in a dark, humidified chamber for 60 minutes.

The final absorbance is read at 660 nm (Table 1) and a standard curve is plotted, the "best fit" curve is computed using Microsoft Excel 98 or similar program. The resulting regression equation is used to calculate biliverdin concentrations (mg/dl) of samples as shown in Table 2. The regression equation utilized to calculate the biliverdin concentrations shown in Table 2 is based on the standard curve generated from the absorbance values in Table 1. This regression equation will, of course, vary from assay as each standard curve will yield a different regression equation for the purposes of calculating biliverdin concentrations in samples.

TABLE 1

Standard curve determination: initial, final, and change in absorbance at 660 nm using water as diluent.

| Biliverdin Standards (mg/dl) | Initial absorbance | Final absorbance | Change in absorbance |
|---|---|---|---|
| 20 | 0.678 | 0.116 | 0.562 |
| 15 | 0.576 | 0.067 | 0.509 |
| 10 | 0.402 | 0.046 | 0.356 |
| 5 | 0.208 | 0.015 | 0.193 |
| 1 | 0.129 | 0 | 0.129 |
| 0.5 | 0.041 | 0 | 0.041 |
| 0.2 | 0.003 | 0 | 0.003 |
| 0.1 | 0.001 | 0 | 0.001 |

TABLE 2

Calculated Biliverdin Concentrations Using Regression Equation established in Chart 1 ($y = 2423.8x^5 - 2113.1x^4 + 262.13x^3 + 166.94x^2 - 76478x$).

| Sample Identification (mg/dl-assay#) | Initial absorbance | Final absorbance | Change in absorbance | Calculated Biliverdin Concentration (mg/dl) |
|---|---|---|---|---|
| 20-1 | 0.674 | 0.117 | 0.557 | 19.4 |
| 15-1 | 0.571 | 0.072 | 0.499 | 14.3 |
| 10-1 | 0.402 | 0.054 | 0.348 | 10.0 |
| 5-1 | 0.2 | 0.015 | 0.185 | 4.0 |
| 1-1 | 0.145 | −0.003 | 0.145 | 2.4 |
| 0.5-1 | 0.049 | −0.007 | 0.049 | 0.0 |
| 0.2-1 | −0.006 | −0.008 | 0 | 0.0 |
| 0.1-1 | −0.009 | −0.001 | 0 | 0.0 |
| 20-2 | 0.67 | 0.118 | 0.552 | 18.8 |
| 15-2 | 0.57 | 0.075 | 0.495 | 14.1 |
| 10-2 | 0.402 | 0.052 | 0.35 | 10.0 |
| 5-2 | 0.201 | 0.014 | 0.187 | 4.1 |
| 1-2 | 0.144 | 0 | 0.144 | 2.4 |
| 0.5-2 | 0.042 | −0.007 | 0.042 | 0.0 |
| 0.2-2 | −0.005 | 0.001 | 0 | 0.0 |
| 0.1-2 | −0.008 | −0.008 | 0 | 0.0 |
| 20-3 | 0.67 | 0.117 | 0.553 | 18.9 |
| 15-3 | 0.585 | 0.069 | 0.516 | 15.4 |
| 10-3 | 0.405 | 0.048 | 0.357 | 10.2 |
| 5-3 | 0.2 | 0.013 | 0.187 | 4.1 |
| 1-3 | 0.142 | −0.006 | 0.142 | 2.3 |
| 0.5-3 | 0.038 | −0.005 | 0.038 | 0.0 |
| 0.2-3 | 0.001 | −0.009 | 0.001 | 0.0 |
| 0.1-3 | −0.008 | −0.007 | 0 | 0.0 |
| 20-4 | 0.668 | 0.12 | 0.548 | 18.3 |
| 15-4 | 0.573 | 0.065 | 0.508 | 14.8 |
| 10-4 | 0.395 | 0.052 | 0.343 | 9.9 |
| 5-4 | 0.205 | 0.013 | 0.192 | 4.3 |
| 1-4 | 0.15 | −0.005 | 0.15 | 2.6 |
| 0.5-4 | 0.039 | −0.007 | 0.039 | 0.0 |
| 0.2-4 | −0.007 | −0.009 | 0 | 0.0 |
| 0.1-4 | −0.003 | −0.009 | 0 | 0.0 |
| 20-5 | 0.676 | 0.118 | 0.558 | 19.5 |
| 15-5 | 0.572 | 0.065 | 0.507 | 14.8 |
| 10-5 | 0.399 | 0.054 | 0.345 | 9.9 |
| 5-5 | 0.199 | 0.012 | 0.187 | 4.1 |
| 1-5 | 0.142 | −0.006 | 0.148 | 2.5 |
| 0.5-5 | 0.04 | −0.011 | 0.051 | 0.1 |
| 0.2-5 | −0.005 | −0.01 | 0.005 | 0.0 |
| 0.1-5 | −0.011 | 0 | 0 | 0.0 |
| 20-6 | 0.666 | 0.118 | 0.548 | 18.3 |
| 15-6 | 0.582 | 0.065 | 0.517 | 15.4 |
| 10-6 | 0.394 | 0.056 | 0.338 | 9.7 |
| 5-6 | 0.203 | 0.012 | 0.191 | 4.3 |
| 1-6 | 0.147 | −0.007 | 0.154 | 2.8 |
| 0.5-6 | 0.04 | 0 | 0.04 | 0.0 |
| 0.2-6 | −0.003 | −0.001 | 0 | 0.0 |
| 0.1-6 | −0.009 | −0.008 | 0 | 0.0 |

The above data was utilized to construct a data plot of calculated biliverdin concentrations (mg/dl) in relation to standard curve values. This plot showed that calculated concentrations agree best with expected concentrations in the range of 10.0 to 20.0 mg/dl, using sterile deionized water as the diluent.

Experiments Utilizing Chicken Serum Diluent:

Protocol:

Standards: Serial dilutions of a 100 mg/dl solution of biliverdin are made, using chicken serum as the diluent.

A reagent blank containing 100 ul sterile chicken serum, 90 ul KP buffer, and 100 ul recombinant rat biliverdin reductase enzyme mix (BVR) is used to zero the instrument at 660 nm. After blanking, the initial absorbance of each standard is measured at 660 nm. Each standard contains:
100 ul of standard
90 ul KP buffer
100 ul BVR After the initial absorbance is measured (Table 3), 10 ul of 0.5 M NADH is added to each cuvette and the solution is gently mixed and incubated at room temperature in a dark, humidified chamber for 60 minutes.

The final absorbance is read at 660 nm (Table 3) and a standard curve is plotted, the "best fit" curve is computed using Microsoft Excel 98 or similar program. The resulting regression equation is used to calculate biliverdin concentrations (mg/dl) of samples (Table 4).

TABLE 3

Standard curve determination: initial, final, and change in absorbance at 660 nm using chicken serum as diluent.

| Biliverdin Standards (mg/dl) | Initial absorbance | Final absorbance | Change in absorbance |
|---|---|---|---|
| 15 | 0.645 | 0.053 | 0.592 |
| 10 | 0.530 | 0.033 | 0.497 |
| 5 | 0.293 | 0.022 | 0.271 |
| 1 | 0.064 | 0.003 | 0.061 |
| 0.5 | 0.021 | 0.000 | 0.021 |

TABLE 4

Calculated Biliverdin Concentrations Using Regression Equation ($y = 260.57x^4 - 207.23x^3 + 48.13x^2 + 15.408x$).

| Sample identification (mg/dl-assay#) | Initial absorbance | Final absorbance | Change in absorbance | Calculated Biliverdin Concentration (mg/dl) |
|---|---|---|---|---|
| 15-1 | 0.636 | 0.056 | 0.580 | 14.2 |
| 10-1 | 0.525 | 0.034 | 0.491 | 9.8 |
| 5-1 | 0.295 | 0.020 | 0.275 | 5.1 |
| 1-1 | 0.064 | 0.002 | 0.062 | 1.1 |
| 0.5-1 | 0.024 | 0.001 | 0.023 | 0.4 |
| 15-2 | 0.632 | 0.056 | 0.576 | 13.9 |
| 10-2 | 0.527 | 0.039 | 0.488 | 9.7 |
| 5-2 | 0.299 | 0.024 | 0.275 | 5.1 |
| 1-2 | 0.063 | 0.013 | 0.050 | 0.9 |
| 0.5-2 | 0.024 | 0.004 | 0.020 | 0.3 |
| 15-3 | 0.641 | 0.061 | 0.580 | 14.2 |
| 10-3 | 0.523 | 0.034 | 0.489 | 9.7 |
| 5-3 | 0.296 | 0.025 | 0.271 | 5.0 |
| 1-3 | 0.066 | 0.000 | 0.066 | 1.2 |
| 0.5-3 | 0.026 | 0.003 | 0.023 | 0.4 |
| 15-4 | 0.639 | 0.062 | 0.577 | 14.0 |
| 10-4 | 0.526 | 0.039 | 0.487 | 9.6 |
| 5-4 | 0.293 | 0.026 | 0.267 | 4.9 |
| 1-4 | 0.063 | 0.006 | 0.057 | 1.0 |

TABLE 4-continued

Calculated Biliverdin Concentrations Using Regression Equation
($y = 260.57x^4 - 207.23x^3 + 48.13x^2 + 15.408x$).

| Sample identification (mg/dl-assay#) | Initial absorbance | Final absorbance | Change in absorbance | Calculated Biliverdin Concentration (mg/dl) |
|---|---|---|---|---|
| 0.5-4 | 0.024 | 0.004 | 0.020 | 0.3 |
| 15-5 | 0.634 | 0.056 | 0.578 | 14.1 |
| 10-5 | 0.526 | 0.040 | 0.486 | 9.6 |
| 5-5 | 0.295 | 0.025 | 0.270 | 5.0 |
| 1-5 | 0.063 | 0.011 | 0.052 | 0.9 |
| 0.5-5 | 0.027 | 0.001 | 0.026 | 0.4 |
| 15-6 | 0.624 | 0.061 | 0.563 | 13.1 |
| 10-6 | 0.521 | 0.042 | 0.479 | 9.4 |
| 5-6 | 0.297 | 0.026 | 0.271 | 5.0 |
| 1-6 | 0.063 | 0.008 | 0.055 | 1.0 |
| 0.5-6 | 0.025 | 0.000 | 0.025 | 0.4 |
| 15-7 | 0.630 | 0.060 | 0.570 | 13.5 |
| 10-7 | 0.514 | 0.041 | 0.473 | 9.2 |
| 5-7 | 0.292 | 0.026 | 0.266 | 4.9 |
| 1-7 | 0.063 | 0.004 | 0.059 | 1.0 |
| 0.5-7 | 0.025 | 0.005 | 0.020 | 0.3 |

The above data was utilized to construct a data plot of calculated biliverdin concentrations (mg/dl) in relation to standard curve values. This plot showed that that calculated concentrations agree best with expected concentrations in the range of 0.5 to 15.0 mg/dl. Chicken serum appears to enhance detection of biliverdin. The remaining validation tests were performed using chicken serum as the diluent (unless otherwise specified).

Comparison of Measurement of Absorbances at Different Wavelengths Used to Plot Standard Curves for Calculation of Biliverdin Concentrations.

Figure 1:
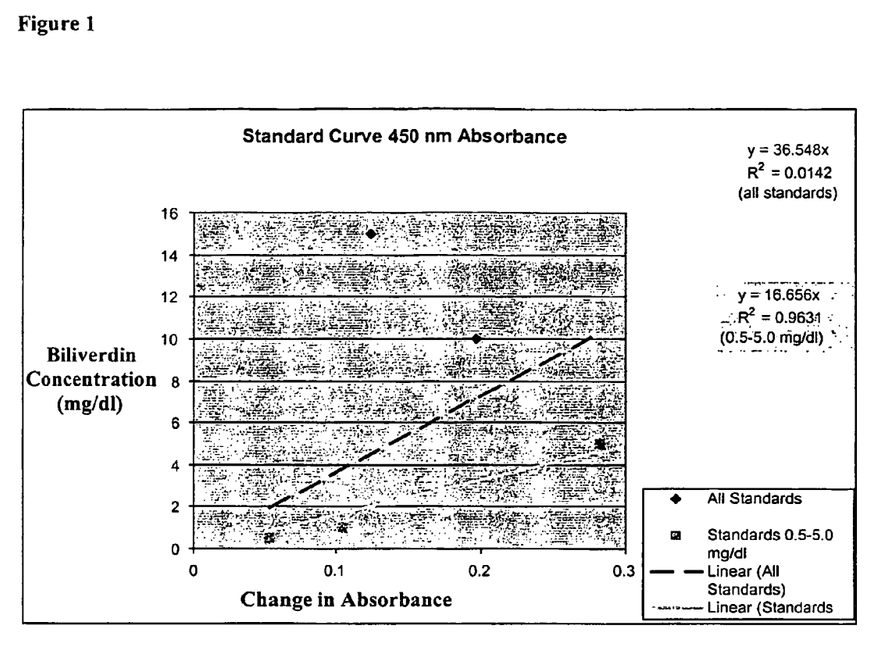
FIG. 1 shows a comparison of linearity between absorbances of all standards vs. 0.5-5.0 mg/dl (linear plot) at 450 nm.
Figure 2:
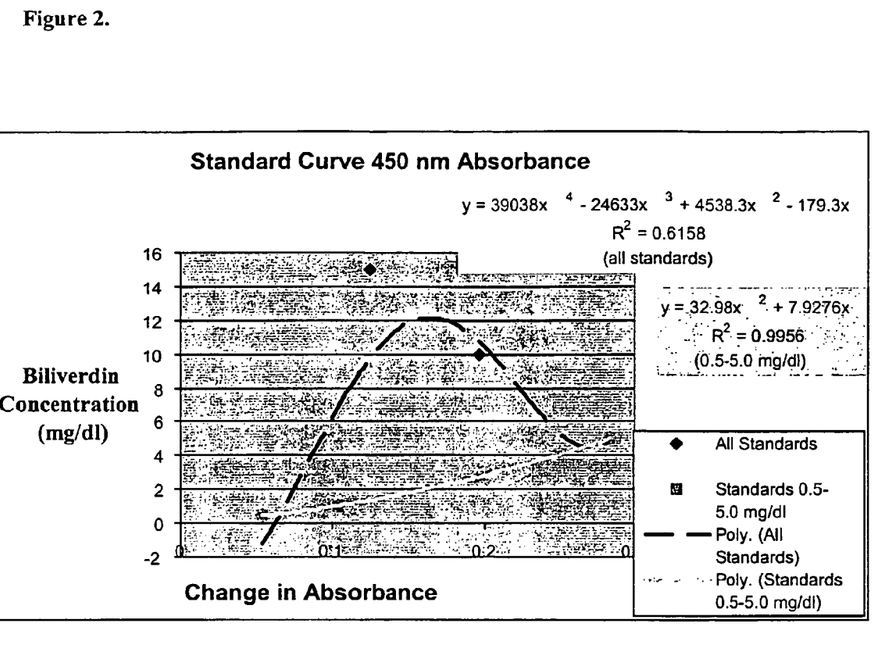
FIG. 2 shows a comparison of linearity between absorbances of all standards vs. 0.5-5.0 mg/dl (polynomial plot) at 450 nm.

Increases in absorbance at 450 and 500 nm were measured. This assay detects increased bilirubin concentrations as biliverdin is reduced to bilirubin by the enzymatic reaction catalyzed by biliverdin reductase. A standard curve was generated and a comparison of linearity between absorbances of all standards vs. 0.5-5.0 mg/dl was performed as shown in FIG. 1. A comparison of linearity between absorbances of all standards vs. 0.5-5.0 mg/dl utilizing a polynomial plot was also performed (FIG. 2).

TABLE 5

Standard curve determination: initial, final, and change in absorbance at 450 nm.

| Biliverdin Standards (mg/dl) | Initial absorbance | Final absorbance | Change in absorbance |
|---|---|---|---|
| 15 | 0.365 | 0.489 | 0.124 |
| 10 | 0.28 | 0.477 | 0.197 |
| 5 | 0.155 | 0.438 | 0.283 |
| 1 | 0.044 | 0.148 | 0.104 |
| 0.5 | 0.021 | 0.074 | 0.053 |

The above data, as plotted in FIGS. 1 and 2, suggests that the "best fit" curve and regression equation, measuring change in absorbance at 450 nm, is from 0.5 to 5.0 mg/dl using a polynomial trendline.

The following sets forth the results obtained when utilizing a wavelength of 500 nm.

TABLE 6

Standard curve determination: initial, final, and change in absorbance at 500 nm.

| Biliverdin Standards (mg/dl) | Initial absorbance | Final absorbance | Change in absorbance |
|---|---|---|---|
| 15 | 0.185 | 0.518 | 0.333 |
| 10 | 0.121 | 0.447 | 0.326 |
| 5 | 0.072 | 0.292 | 0.22 |
| 1 | 0.026 | 0.072 | 0.046 |
| 0.5 | 0.018 | 0.037 | 0.019 |

Figure 3:
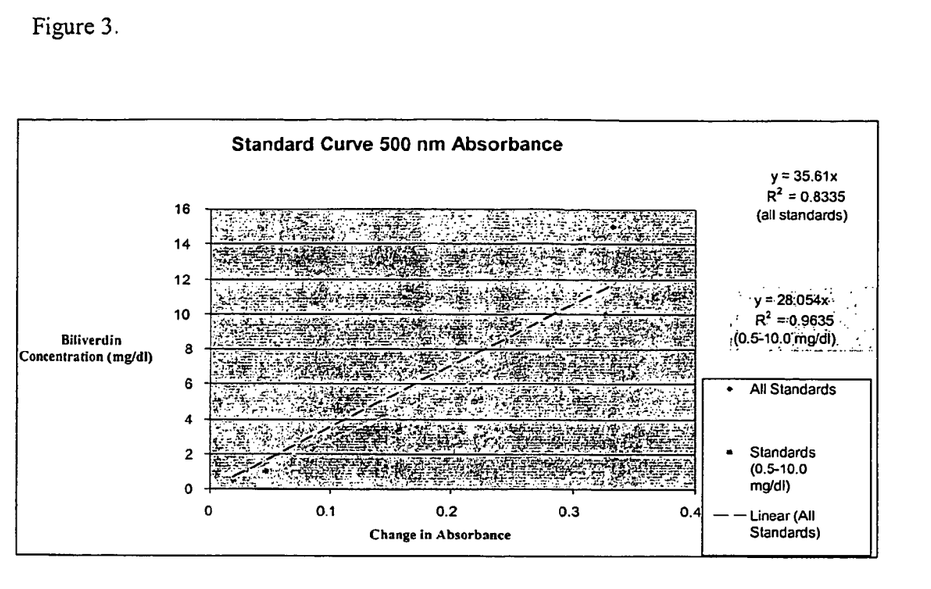
FIG. 3 shows a comparison of linearity between absorbances of all standards vs. 0.5-10.0 mg/dl (linear plot) at 500 nm.
Figure 4:
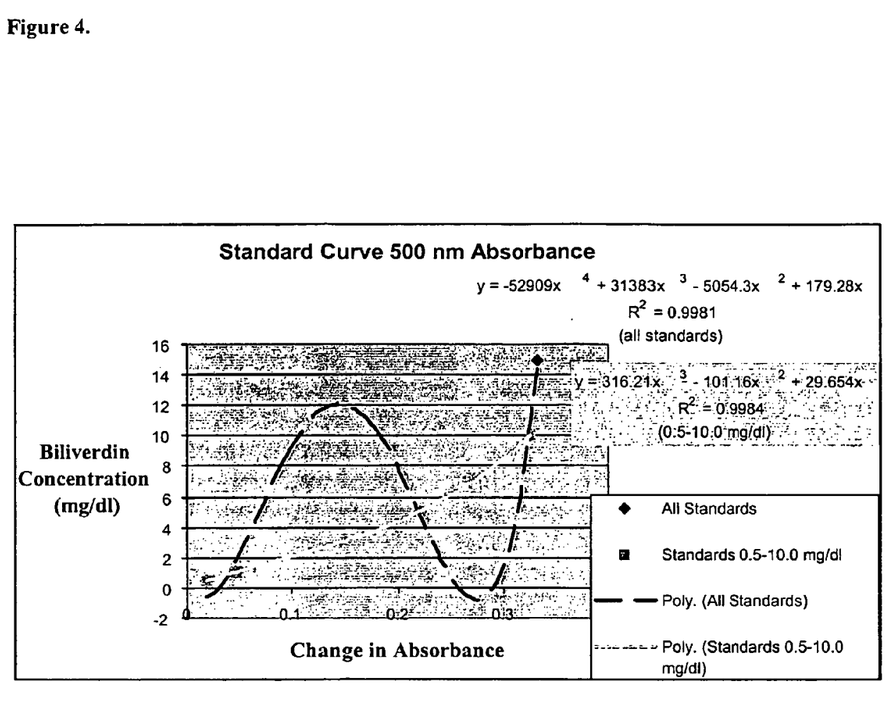
FIG. 4 shows a comparison of linearity between absorbances of all standards vs. 0.5-10.0 mg/dl (polynomial plot) at 500 nm.
Figure 5:
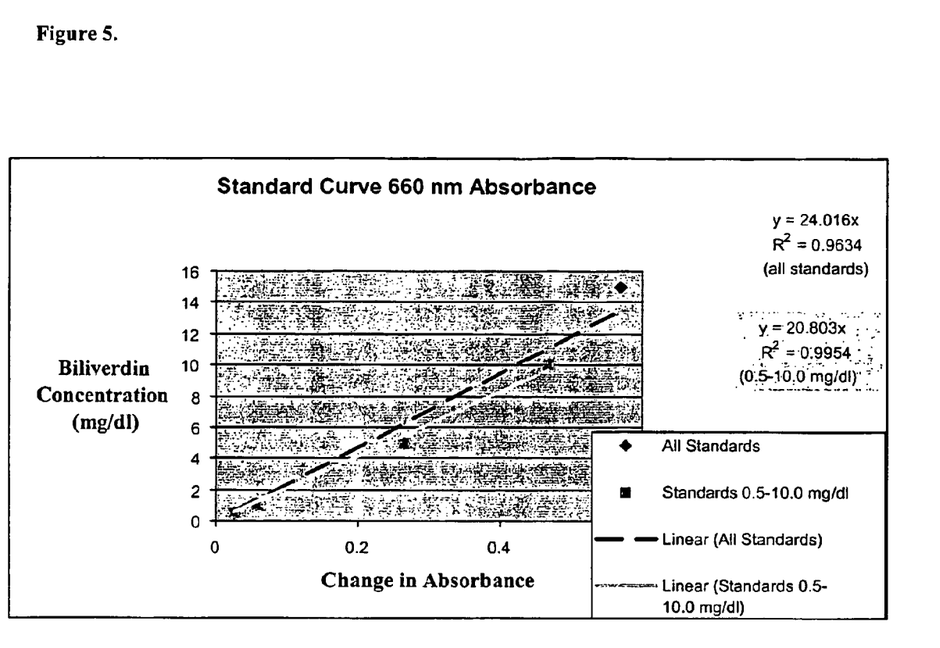
FIG. 5 shows a comparison of linearity between absorbances of all standards vs. 0.5-10.0 mg/dl (linear plot) at 660 nm.
Figure 6:
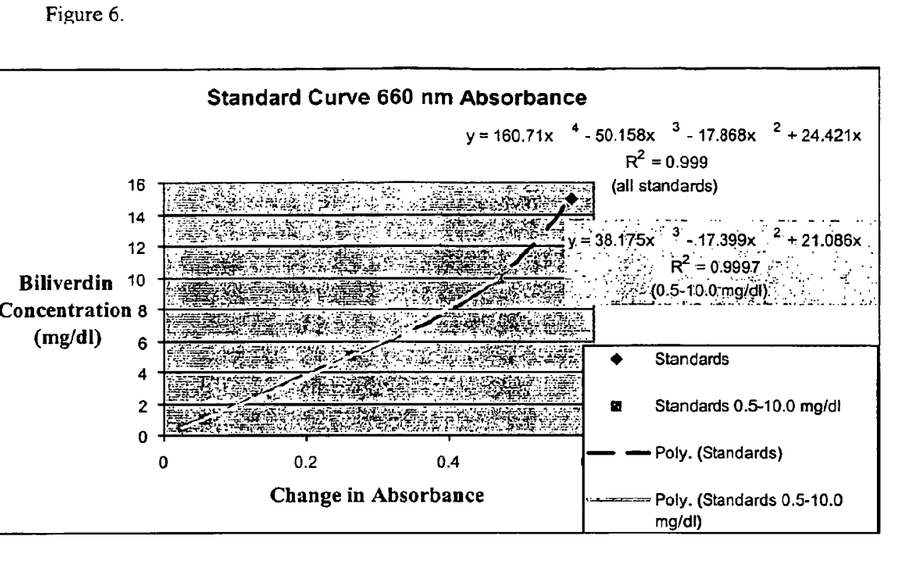
FIG. 6 shows a comparison of linearity between absorbances of all standards vs. 0.5-10.0 mg/dl (polynomial plot) at 660 nm.

The above data, as plotted in FIGS. 3 and 4, suggests that the "best fit" curve and regression equation, measuring change in absorbance at 500 nm, is from 0.5 to 10.0 mg/dl using a polynomial trendline.

The following sets forth the results obtained when utilizing a wavelength of 660 nm.

TABLE 7

Standard curve determination: initial, final, and change in absorbance at 660 nm.

| Biliverdin Standards (mg/dl) | Initial absorbance | Final absorbance | Change in absorbance |
|---|---|---|---|
| 15 | 0.619 | 0.051 | 0.568 |
| 10 | 0.508 | 0.04 | 0.468 |
| 5 | 0.288 | 0.025 | 0.263 |
| 1 | 0.061 | 0.004 | 0.057 |
| 0.5 | 0.026 | 0.001 | 0.025 |

The above data, as plotted in FIGS. 3 and 4, suggests that measuring decreases in absorbance at 660 nm produces a "best fit" polynomial curve from 0.5-15.0 mg/dl. Although other assays remain valid for measurement of biliverdin concentration, this assay offers the widest range of determining biliverdin concentrations for establishment of reference intervals.

Intra- and interassay validations were determined by measuring changes in absorbance at a wavelength of 660 nm. The regression equation: $y=260.57x^4-207.23x^3+48.13x^2+15.408x$, based on a standard curve that was generated and utilized to obtain the biliverdin concentrations in Table 4 and with an $R^2$ value of 0.9998, was used for intra- and interassays. The data in Table 4 also represent the same day interassay validation.

Determination of Within Run (Within Assay, Intra-Assay), Same Day Interassay, and Day-To-Day Interassay Precision.

To minimize technical errors, master mixes of each standard (0.5, 1.0, 5.0, 10.0, 15.0 mg/dl) were made for each assay. Total volume of the master mixes was sufficient for enough sample volume per individual test plus one additional test. The master mixes were composed of the appropriate biliverdin standard diluted in chicken serum, KP buffer, and BVR. The biliverdin assay was performed and the concentrations of biliverdin were calculated as previously described (change in absorbance at 660 nm using standard curve/regression equation in Table 3). Master mixes were used immediately, were refrigerated at 4° C. between same day interassay runs, and frozen at −20° C. between day-to-day interassay runs.

Determination of Intra-Assay Precision

TABLE 8

Statistical analysis of biliverdin intra-assay.

| Expected Value (mg/dl) | | Range | Mean | 1 × s.d. | 2 × s.d. | Systematic Error | Total Error | CV (%) |
|---|---|---|---|---|---|---|---|---|
| 15 | Calculated value (mg/dl) | 12.8-13.9 | 13.3 | 0.337 | 0.673 | 1.7 | 2.37 | 2.53 |
| 10 | Calculated value (mg/dl) | 9.5-9.7 | 9.6 | 0.090 | 0.180 | 0.4 | 0.580 | 0.94 |
| 5.0 | Calculated value (mg/dl) | 4.7-4.9 | 4.8 | 0.058 | 0.115 | 0.2 | 0.315 | 1.20 |
| 1.0 | Calculated value (mg/dl) | 0.9-1.0 | 0.9 | 0.053 | 0.107 | 0.1 | 0.207 | 5.67 |
| 0.5 | Calculated value (mg/dl) | 0.2-0.4 | 0.3 | 0.076 | 0.151 | 0.2 | 0.351 | 23.01 | s.d.: standard deviation
systematic error = |mean-expected value|
total error = 2 s.d. + systematic error
CV = coefficient of variation (s.d./mean) × 100

Determination of Same Day Interassay Precision

TABLE 9

Statistical analysis of biliverdin same day interassay.

| Expected Value (mg/dl) | | Range | Mean | 1 × s.d. | 2 × s.d. | Systematic Error | Total Error | CV (%) |
|---|---|---|---|---|---|---|---|---|
| 15 | Calculated value (mg/dl) | 13.1-14.2 | 13.9 | 0.412 | 0.823 | 1.1 | 1.923 | 2.97 |
| 10 | Calculated value (mg/dl) | 9.2-9.8 | 9.6 | 0.206 | 0.412 | 0.4 | 0.812 | 2.15 |
| 5.0 | Calculated value (mg/dl) | 4.9-5.1 | 5.0 | 0.082 | 0.163 | 0.0 | 0.163 | 1.63 |
| 1.0 | Calculated value (mg/dl) | 0.9-1.2 | 1.0 | 0.107 | 0.214 | 0.0 | 0.214 | 10.54 |
| 0.5 | Calculated value (mg/dl) | 0.3-0.4 | 0.4 | 0.053 | 0.107 | 0.1 | 0.207 | 14.97 | s.d.: standard deviation
systematic error = |mean-expected value|
total error = 2 s.d. + systematic error
CV = coefficient of variation (s.d./mean) × 100

Determination of Day-To-Day Interassay Precision

TABLE 10

Statistical analysis of biliverdin day-to-day interassay.

| Expected Value (mg/dl) | | Range | Mean | 1 × s.d. | 2 × s.d. | Systematic Error | Total Error | CV (%) |
|---|---|---|---|---|---|---|---|---|
| 15 | Calculated value (mg/dl) | 11.9-13.4 | 12.8 | 0.763 | 1.526 | 2.22 | 3.75 | 5.97 |
| 10 | Calculated value (mg/dl) | 8.7-9.6 | 9.2 | 0.378 | 0.756 | 0.84 | 1.60 | 4.13 |
| 5.0 | Calculated value (mg/dl) | 4.6-5.1 | 4.8 | 0.212 | 0.424 | 0.20 | 0.62 | 4.42 |
| 1.0 | Calculated value (mg/dl) | 1.0 | 1.0 | 0.000 | 0.000 | 0.00 | 0.00 | 0.00 |
| 0.5 | Calculated value (mg/dl) | 0.3-0.4 | 0.4 | 0.045 | 0.089 | 0.12 | 0.21 | 11.77 | s.d.: standard deviation
systematic error = |mean-expected value|
total error = 2 s.d. + systematic error
CV = coefficient of variation (s.d./mean) × 100

Measurement of Biliverdin Concentrations in Avian and Reptilian Body Fluids

A standard curve was used to determine the "best fit" regression equation as described above. This equation was subsequently used to calculate the biliverdin concentration in clinical samples.

TABLE 11

Computation of Standard Curve

| Biliverdin Standards (mg/dl) | Initial absorbance | Final absorbance | Change in absorbance |
|---|---|---|---|
| 15 | 0.645 | 0.140 | 0.505 |
| 10 | 0.527 | 0.153 | 0.374 |
| 5 | 0.315 | 0.050 | 0.265 |
| 1 | 0.078 | 0.052 | 0.026 |
| 0.5 | 0.076 | 0.039 | 0.017 |

TABLE 12

Calculated Serum Biliverdin Concentrations in Avian and Reptilian Body Fluids utilizing regression equation ($y = -1262.3x^4 + 1238.1x^3 - 328.74x^2 + 42.537x$)
$R^2 = 0.9998$

| Sample Identification | Initial Absorbance | Final Absorbance | Change in absorbance | Calculated Biliverdin concentration (mg/dl) | Reported Value (mg/dl) |
|---|---|---|---|---|---|
| Iguana coelomic fluid | 0.059 | 0.036 | 0.023 | 0.8 | 0.8 |
| Psittacine urine | 0.291 | 0.082 | 0.209 | 3.4 | 3.4 |
| Turtle serum | 0.634 | 0.65 | −0.016 | −0.8 | ≦0.5 |
| Great horned owl serum | 0.072 | 0.083 | −0.011 | −0.5 | ≦0.5 |
| 5 mg/dl control | 0.31 | 0.062 | 0.248 | 4.4 | 4.4 |
| Military macaw serum | 0.179 | 0.2 | −0.021 | −1.0 | ≦0.5 |
| Owl serum | 0.111 | 0.124 | −0.013 | −0.6 | ≦0.5 |
| Yellow-naped Amazon parrot serum | 0.071 | 0.014 | 0.057 | 1.6 | 1.6 |
| Toucan serum | 0.001 | 0.031 | −0.03 | −1.6 | ≦0.5 |
| 10 mg/dl control | 0.494 | 0.089 | 0.405 | 11.6 | 11.6 |
| Psittacine coelomic fluid | 0.069 | 0.091 | −0.022 | −1.1 | ≦0.5 |
| Loggerhead turtle serum | 0.137 | 0.027 | 0.11 | 2.2 | 2.2 |
| Psittacine serum | 0.426 | 0.438 | −0.012 | −0.6 | ≦0.5 |
| Psittacine urine | 0.211 | 0.072 | 0.139 | 2.4 | 2.4 |
| 1 mg/dl control | 0.077 | 0.032 | 0.045 | 1.4 | 1.4 |
| Psittacine serum | 0.09 | 0.042 | 0.048 | 1.4 | 1.4 |
| Tortoise serum | 0.05 | 0.04 | 0.01 | 0.4 | ≦0.5 |
| 0.5 mg/dl control | 0.05 | 0.031 | 0.019 | 0.7 | 0.7 |
| Cockatoo serum | 0 | 0.03 | −0.03 | −1.6 | ≦0.5 |
| Tortoise serum | 0.004 | 0.012 | −0.008 | −0.4 | ≦0.5 |

Calculated Serum Biliverdin Concentrations in Loggerhead Turtle and Psittacine Bird Serum

TABLE 13

Computation of Standard Curve

| Biliverdin Standards (mg/dl) | Initial absorbance | Final absorbance | Change in absorbance |
|---|---|---|---|
| 15 | 0.659 | 0.165 | 0.494 |
| 10 | 0.599 | 0.220 | 0.379 |
| 5 | 0.430 | 0.199 | 0.231 |
| 1 | 0.197 | 0.113 | 0.084 |
| 0.5 | 0.167 | 0.143 | 0.024 |

TABLE 14

Calculated Serum Biliverdin Concentrations in Loggerhead Turtle and Psittacine Bird Serum calculated utilizing regression equation (y = 152.84x4 − 168.12x3 + 92.948x2 + 7.0412x) $R^2$ = 0.9993. Loggerhead turtle samples are preceded by "CC."

| Sample Identification | Initial absorbance | Final absorbance | Change in absorbance | Calculated Biliverdin Concentration (mg/dl) | Reported Valu (mg/dl) |
|---|---|---|---|---|---|
| CC 2126 | 0.250 | 0.131 | 0.119 | 1.9 | 1.9 |
| CC 4108 | 0.202 | 0.110 | 0.092 | 1.3 | 1.3 |
| CC 4109 | 0.163 | 0.091 | 0.072 | 0.9 | 0.9 |
| CC 4110 | 0.177 | 0.092 | 0.085 | 1.2 | 1.2 |
| CC 4111 | 0.162 | 0.083 | 0.079 | 1.1 | 1.1 |
| CC 4112 | 0.175 | 0.085 | 0.090 | 1.3 | 1.3 |
| CC 4113 | 0.161 | 0.083 | 0.078 | 1.0 | 1.0 |
| CC 4114 | 0.186 | 0.112 | 0.074 | 1.0 | 1.0 |
| CC 4116 | 0.185 | 0.055 | 0.130 | 2.2 | 2.2 |
| CC 4117 | 0.201 | 0.276 | −0.075 | 0.1 | ≦0.5 |
| CC 4118 | 0.199 | 0.112 | 0.087 | 1.2 | 1.2 |
| CC 4119 | 0.284 | 0.180 | 0.104 | 1.6 | 1.6 |
| Control 1.0 | 0.192 | 0.138 | 0.054 | 0.6 | 0.6 |
| Control 10.0 | 0.582 | 0.169 | 0.413 | 11.4 | 11.4 |
| CC 4120 | 0.177 | 0.114 | 0.063 | 0.8 | 0.8 |
| CC 4121 | 0.264 | 0.289 | −0.025 | −0.1 | ≦0.5 |
| CC 4122 | 0.226 | 0.107 | 0.119 | 1.9 | 1.9 |
| CC 4123 | 0.198 | 0.104 | 0.094 | 1.4 | 1.4 |
| CC 4124 | 0.194 | 0.112 | 0.082 | 1.1 | 1.1 |
| CC 4125 | 0.256 | 0.123 | 0.133 | 2.2 | 2.2 |
| CC 4131 | 0.284 | 0.174 | 0.110 | 1.7 | 1.7 |
| CC 4132 | 0.183 | 0.130 | 0.053 | 0.6 | 0.6 |
| CC 4133 | 0.347 | 0.214 | 0.133 | 2.2 | 2.2 |
| CC 4134 | 0.206 | 0.127 | 0.079 | 1.1 | 1.1 |
| CC 4135 | 0.251 | 0.111 | 0.140 | 2.4 | 2.4 |
| CC 4136 | 0.207 | 0.096 | 0.111 | 1.7 | 1.7 |
| Control 0.5 | 0.179 | 0.136 | 0.043 | 0.5 | 0.5 |
| Control 1.0 | 0.200 | 0.142 | 0.058 | 0.7 | 0.7 |
| CC 4138 | 0.182 | 0.143 | 0.039 | 0.4 | ≦0.5 |
| CC 4140 | 0.308 | 0.160 | 0.148 | 2.6 | 2.6 |
| CC 4141 | 0.203 | 0.094 | 0.109 | 1.7 | 1.7 |
| CC 4142 | 0.208 | 0.100 | 0.108 | 1.7 | 1.7 |
| CC 4143 | 0.342 | 0.170 | 0.172 | 3.2 | 3.2 |
| CC 4144 | 0.212 | 0.153 | 0.059 | 0.7 | 0.7 |
| CC 4145 | 0.375 | 0.212 | 0.163 | 3.0 | 3.0 |
| CC 4146 | 0.217 | 0.174 | 0.043 | 0.5 | 0.5 |
| CC 4147 | 0.207 | 0.140 | 0.067 | 0.8 | 0.8 |
| CC 4148 | 0.511 | 0.164 | 0.347 | 8.8 | 8.8 |
| CC 4149 | 0.299 | 0.129 | 0.170 | 3.2 | 3.2 |
| CC 4151 | 0.307 | 0.156 | 0.151 | 2.7 | 2.7 |
| Control 10.0 | 0.562 | 0.175 | 0.387 | 10.3 | 10.3 |
| Control 0.5 | 0.195 | 0.140 | 0.055 | 0.6 | 0.6 |
| Macaw sp. | 0.117 | 0.126 | −0.009 | −0.1 | ≦0.5 |
| Hyacinth macaw | 0.224 | 0.197 | 0.027 | 0.3 | ≦0.5 |
| Scarlet Macaw | 0.405 | 0.395 | 0.010 | 0.1 | ≦0.5 |
| Thickbilled parrot | 0.197 | 0.178 | 0.019 | 0.2 | ≦0.5 |
| Buffon's macaw | 0.202 | 0.178 | 0.024 | 0.2 | ≦0.5 |
| Major Mitchell cockatoo | 0.100 | 0.095 | 0.005 | 0.0 | ≦0.5 |
| Control 10.0 | 0.590 | 0.158 | 0.432 | 12.2 | 12.2 |
| Control 15.0 | 0.657 | 0.188 | 0.469 | 13.8 | 13.8 |
| Eclectus parrot | 0.242 | 0.248 | −0.006 | 0.0 | ≦0.5 |
| Caninde macaw | 0.168 | 0.151 | 0.017 | 0.1 | ≦0.5 |
| Severe macaw | 0.216 | 0.110 | 0.106 | 1.6 | 1.6 |
| *Psitticula* Derbian | 0.176 | 0.142 | 0.034 | 0.3 | ≦0.5 |
| Control 5.0 | 0.387 | 0.120 | 0.267 | 6.1 | 6.1 |
| Control 0.5 | 0.138 | 0.107 | 0.031 | 0.3 | ≦0.5 |
| Control 1.0 | 0.167 | 0.117 | 0.050 | 0.6 | 0.6 |
| Macaw sp. | 0.184 | 0.179 | 0.005 | 0.0 | ≦0.5 |
| Scarlet macaw | 0.146 | 0.099 | 0.047 | 0.5 | ≦0.5 |
| Blue and gold macaw | 0.197 | 0.199 | −0.002 | 0.0 | ≦0.5 |
| Palm cockatoo | 0.127 | 0.127 | 0.000 | 0.0 | ≦0.5 |
| Control 0.5 | 0.139 | 0.100 | 0.039 | 0.4 | ≦0.5 |
| Control 1.0 | 0.156 | 0.097 | 0.059 | 0.7 | 0.7 |
| Control 5.0 | 0.385 | 0.150 | 0.235 | 5.1 | 5.1 |
| Palm cockatoo | 0.263 | 0.227 | 0.036 | 0.4 | ≦0.5 |
| Palm cockatoo | 0.210 | 0.167 | 0.043 | 0.5 | ≦0.5 |
| Palm cockatoo | 0.367 | 0.296 | 0.071 | 0.9 | 0.9 |
| Palm cockatoo | 0.455 | 0.422 | 0.033 | 0.3 | ≦0.5 |
| Umbrella cockatoo | 0.372 | 0.102 | 0.270 | 6.2 | 6.2 |
| Severe macaw | 0.341 | 0.309 | 0.032 | 0.3 | ≦0.5 |

TABLE 14-continued

Calculated Serum Biliverdin Concentrations in Loggerhead Turtle and Psittacine Bird Serum calculated utilizing regression equation (y = 152.84x4 − 168.12x3 + 92.948x2 + 7.0412x) $R^2$ = 0.9993. Loggerhead turtle samples are preceded by "CC."

| Sample Identification | Initial absorbance | Final absorbance | Change in absorbance | Calculated Biliverdin Concentration (mg/dl) | Reported Valu (mg/dl) |
|---|---|---|---|---|---|
| Control 10.0 | 0.563 | 0.170 | 0.393 | 10.6 | 10.6 |
| Control 15.0 | 0.640 | 0.166 | 0.474 | 14.0 | 14.0 |

Throughout this application, various publications are referenced. The disclosures of these publications in their entireties are hereby incorporated by reference into this application in order to more fully describe the state of the art to which this invention pertains.

Although the present process has been described with reference to specific details of certain embodiments thereof, it is not intended that such details should be regarded as limitations upon the scope of the invention except as and to the extent that they are included in the accompanying claims.

REFERENCES

1. Ennis O, Maytum R, and Mantle T J. 1997. Cloning and overexpression of rat kidney biliverdin IXα reductase as a fusion protein with glutathione S-transferase: stereochemistry of NADH oxidation and evidence that the presence of the glutathione S-transferase domain does not effect BVR-A activity. Biochem J 328:33-36.
2. Kutty R K and Maines M D. 1981. Purification and characterization of biliverdin reductase from rat liver. J Biol Chem 256: 3956-3962.
3. Fakhrai H and Maines M D. 1992. Expression and characterization of a cDNA for rat kidney biliverdin reductase: evidence suggesting the liver and kidney enzymes are the same transcript product. J Biol Chem 267: 4023-4029.
4. Cunningham O, Dunne A, Sabio P, Lightner D, Mantle T J. 2000. Studies on the specificity of the tetrapyrrole substrate for human biliverdin-IXα reductase and biliverdin-IXβ reductase. Journal of Biological Chemistry 275(25): 19009-19017.
5. Harr K E. 2002. Clinical chemistry of companion avian species: a review. Veterinary Clinical Pathology 31(3):140-151. p. 145: "Biliverdin (the tetrapyrrole dehydrobilirubin) can be measured in research laboratories (Itoh, et al.) by high performance liquid chromatography but currently is not measured in clinical laboratories."
6. Itoh S, Kondo M, Imai T, Kusaka T, Isobe K, Onishi S. 2001. Relationships between serum (ZZ)-bilirubin, its subfractions and biliverdin concentrations in infants at 1-month check-ups. Ann Clin Biochem. 38(Pt 4):323-8.

What is claimed is:

1. A method of detecting hepatic function in an avian or reptilian subject, comprising:
    detecting substantially all of the biliverdin in a sample comprising
    (a) contacting a sample from an avian or reptilian subject with biliverdin reductase;
    (b) measuring a change in an absorbance value in at least one wavelength between about 325 to about 750 nm; and
    (c) calculating the amount of substantially all of the biliverdin in the sample by comparing the changes in absorbance with absorbance values for known biliverdin amounts.

2. The method of claim 1, wherein measuring a change in an absorbance value in at least one wavelength comprises detecting the absorbance value at two fixed time points.

3. The method of claim 1, wherein measuring a change in an absorbance value in at least one wavelength comprises detecting the absorbance value continuously.

4. The method of claim 1, wherein the at least one wavelength is about 450, about 500, or about 660 nm.

5. The method of claim 1, wherein the sample from an avian or reptilian subject is derived from blood, serum, urine, sputum, or fine needle aspirations.

6. The method of claim 1, further comprising repeating steps (a)-(c) at least one time to obtain at least a second biliverdin amount, and assessing hepatic function by comparing the first biliverdin amount with at least a second biliverdin amount.

7. The method of claim 6, wherein the at least one wavelength is about 450, about 500, or about 660 nm.

8. The method of claim 1, wherein when the amount of substantially all of the biliverdin in the sample is greater than or less than normal biliverdin amounts for that subject's species, the subject is diagnosed with a hepatic disease.

9. The method of claim 8, wherein the hepatic disease is hepatocellular swelling, hepatic fibrosis, hepatic inflammation, red cell hemolysis, bile duct inflammation or obstruction, erythrocyte destruction, or hemoglobin degradation.

10. A method of detecting hepatic function in an avian or reptilian subject, comprising:
    (a) contacting a sample from an avian or reptilian subject with biliverdin reductase;
    (b) measuring a change in an absorbance value in at least two wavelengths between about 325 nm to about 750 nm, and
    (c) calculating the amount of substantially all of the biliverdin in a sample by comparing the changes in absorbance with absorbance values for known biliverdin amounts.

11. The method of claim 10, wherein measuring a change in an absorbance value in at least two wavelengths comprises detecting the absorbance value at two fixed time points.

12. The method of claim 10, wherein measuring a change in an absorbance value in at least two wavelengths comprises detecting the absorbance value continuously.

13. The method of claim 10, wherein one of the at least two wavelengths is about 450 nm, about 500 nm, or about 660 nm.

14. The method of claim 10, wherein one of the at least two wavelengths is about 450 and a second wavelength is about 660 nm.

15. The method of claim 10, wherein the sample from an avian or reptilian subject is derived from blood, serum, urine, sputum, or fine needle aspirations.

16. The method of claim 10, further comprising repeating steps (a)-(c) at least one time to obtain at least a second biliverdin amount, and assessing hepatic function by comparing the first biliverdin amount with at least a second biliverdin amount.

17. The method of claim 16, wherein one of the at least two wavelengths is about 450 nm, about 500 nm, or about 660 nm.

18. The method of claim 10, wherein when the amount of substantially all of the biliverdin in the sample is greater than or less than normal biliverdin amounts for that subject's species, the subject is diagnosed with a hepatic disease.

19. A method of monitoring the efficacy of drug therapy in an avian or reptilian subject, comprising:
    detecting hepatic function in an avian or reptilian subject undergoing drug therapy comprising
    (a) contacting a sample from an avian or reptilian subject with biliverdin reductase;
    (b) measuring a change in an absorbance value in at least one wavelength between about 325 to about 750 nm,
    (c) calculating the amount of substantially all of the biliverdin in a sample by comparing the changes in absorbance with absorbance values for known biliverdin amounts to obtain a first biliverdin amount;
    (d) repeating steps (a)-(c) at least one time to obtain at least a second biliverdin amount;
    assessing hepatic function by comparing the first biliverdin amount with the at least a second biliverdin amount; and
    if required, adjusting at least one aspect of the drug therapy selected from the group consisting of changing the drug, the dose, and the frequency of the drug therapy.

* * * * *

SEQUENCE LISTING

<160> NUMBER OF SEQ ID NOS: 2

<210> SEQ ID NO 1
<211> LENGTH: 39
<212> TYPE: DNA
<213> ORGANISM: Artificial Sequence
<220> FEATURE:
<223> OTHER INFORMATION: Description of Artificial Sequence; note = synthetic construct

<400> SEQUENCE: 1
ggggtacccc gactgaagag accgccatgg atgccgagc                              39

<210> SEQ ID NO 2
<211> LENGTH: 40
<212> TYPE: DNA
<213> ORGANISM: Artificial Sequence
<220> FEATURE:
<223> OTHER INFORMATION: Description of Artificial Sequence; note = synthetic construct

<400> SEQUENCE: 2
gctctagagc gacatgttcc atggtaagag ctaaaggtga                             40